US008676296B2

(12) United States Patent
Park et al.

(10) Patent No.: US 8,676,296 B2
(45) Date of Patent: Mar. 18, 2014

(54) ECHO-SPECIFIC K-SPACE REORDERING APPROACH TO COMPATIBLE DUAL-ECHO ARTERIOVENOGRAPHY

(75) Inventors: Sung-Hong Park, Pittsburgh, PA (US); Kyongtae Ty Bae, Pittsburgh, PA (US)

(73) Assignee: Univerity of Pittsburgh—Of The Commonwealth System of Higher Education, Pittsburgh, PA (US)

( * ) Notice: Subject to any disclaimer, the term of this patent is extended or adjusted under 35 U.S.C. 154(b) by 311 days.

(21) Appl. No.: 13/062,187

(22) PCT Filed: Sep. 14, 2009

(86) PCT No.: PCT/US2009/005131
§ 371 (c)(1),
(2), (4) Date: May 4, 2011

(87) PCT Pub. No.: WO2010/030389
PCT Pub. Date: Mar. 18, 2010

(65) Prior Publication Data
US 2011/0213237 A1    Sep. 1, 2011

Related U.S. Application Data

(60) Provisional application No. 61/097,145, filed on Sep. 15, 2008.

(51) Int. Cl.
*A61B 5/05* (2006.01)
(52) U.S. Cl.
USPC .......................................... 600/419; 600/410
(58) Field of Classification Search
USPC ........................................................ 600/419
See application file for complete search history.

(56) References Cited

U.S. PATENT DOCUMENTS

| | | |
|---|---|---|
| 6,192,264 B1 | 2/2001 | Foo et al. |
| 2006/0161060 A1* | 7/2006 | Pai ................................. 600/431 |
| 2008/0039726 A1 | 2/2008 | Perry et al. |
| 2008/0119879 A1 | 5/2008 | Brenneman et al. |

OTHER PUBLICATIONS

"Du et al.," "Simultaenous acquisition of MR angiography and venography (MRAV)," Magnetic Resonance in Medicine, vol. 59, Issue 5, pp. 954-958, May 2008.*
International Search Report PCT/US2009/005131 dated Apr. 12, 2010.

* cited by examiner

*Primary Examiner* — Tse Chen
*Assistant Examiner* — Patricia Park
(74) *Attorney, Agent, or Firm* — Foley & Lardner LLP (57) ABSTRACT

A dual-echo sequence technique provided herein empowers simultaneous acquisition of both TOF MRA and BOLD MRV in a single MR acquisition. By this approach, an echo-specific K-space ordering scheme permits the adjustment of the scan parameters that are compatible for each of the MRA and MRV. The image quality in the MRA and MRV acquired by this compatible dual-echo arteriovenography (CODEA) technique is comparable to that for conventional, single-echo MRA and MRV. When the technique is integrated with MOTSA, seamless vascular connectivity is achieved in both MRA and MRV over a large area of brain anatomy. The technique will facilitate routine clinical acquisition and application of dual-echo MRA and MRV, as both MRA and MRV can be acquired with minimal impact on the image quality and without adversely affecting the scan throughput.

7 Claims, 7 Drawing Sheets

ECHO-SPECIFIC K-SPACE REORDERING APPROACH TO COMPATIBLE DUAL-ECHO ARTERIOVENOGRAPHY

CROSS-REFERENCE TO RELATED PATENT APPLICATIONS

This application claims priority from U.S. Provisional Application Ser. No. 61/097,145, filed Sep. 15, 2008, which is incorporated herein by reference in its entirety.

BACKGROUND OF THE INVENTION

All of the references cited herein are incorporated by references in their entirety.

MR angiography (MRA) that is based on the time-of-flight (TOF) contrast provides detailed anatomy of arterial vasculature and is routinely used in clinical brain imaging. As a complementary vascular imaging modality, MR venography (MRV) that is based on blood oxygenation level dependent (BOLD) contrast has been used clinically to delineate venous vascular anatomy in the brain.

Because MRA and MRV depict different neuronal and vascular abnormalities in brain diseases, it is desirable to acquire both MRA and MRV in clinical brain imaging studies. Nevertheless, both MRA (based on TOF contrast) and MRV (based on BOLD contrast) require relatively long scan duration, typically 5-15 minutes for each method. Accordingly, acquisition of both MRA and MRV in routine clinical brain imaging studies would prolong the total imaging time, reduce the MR examination throughput, and limit patient compliance. As a result, MRV is not routinely performed in clinical brain imaging examinations.

Recent studies have reported technical developments relating to simultaneous acquisition of both (TOF-based) MRA and (BOLD-based) MRV using the scan time required for the acquisition of only one, MRA or MRV. Du and Jin, *Magnetic Resonance in Medicine*, 59: 954 (2008); Barnes et al., *Proc. Int'l. Soc. Mag. Reson. Med.*, 16: 2231 (2008). Despite this considerable advance, however, technical challenges remain in simultaneous acquisition of MRA and MRV due to conflicting scan conditions required for the optimization of MRA and MRV. On one hand, MRA necessitates the application of a ramped excitation pulse with higher flip angle, magnetization transfer contrast (MTC) pulse, spatial pre-saturation pulse, and shorter echo time (TE) for better inflow enhancement. On the other hand, MRV requires a flat excitation pulse with lower flip angle, no preparation pulse, longer TE, and low acquisition bandwidth for better $T_2^*$ contrast.

These conflicting scan parameter requirements for the optimization of MRA and MRV image quality are not readily counterbalanced or reconciled in conventional methods for simultaneous acquisition of MRA and MRV. For example, in the dual-echo method proposed by Du and Jin (2008), supra, the radio frequency (RF) pulse conditions (i.e., excitation RF profile, flip angle, spatial presaturation pulse, MTC pulse) were not adjustable between the acquisitions of MRA and MRV. Consequently, the vascular contrast of the MRA and MRV could not be optimized.

SUMMARY OF THE INVENTION

Accordingly, the present invention provides a dual-echo method related to an echo-specific K-space ordering scheme for simultaneously acquiring both TOF MRA and BOLD MRV in a single MRI acquisition, thereby allowing both MRA and MRV to be acquired during routine clinical acquisition and application of dual-echo MRA and MRV with minimal impact on the image quality and without adversely affecting the scan throughput. The present invention can be applied to examine any suitable biological tissue or organ, including a brain, for example.

Pursuant to one embodiment of the invention, the method comprises the steps of: (A) separating the center regions for a first and a second echo in K-space from each other; and then (B) acquiring the angiography and the venography from the first and second echoes, respectively, by applying pre-defined K-space scan parameters that are specific to the center regions for the two echoes in K-space. In this context, the scan parameters for the first echo are independent from those for the second echo.

In one embodiment, the design of the scan parameters (collectively, the "scan protocol") is such that the center regions for the two echoes are maximally separated from each other. The separation can be along a phase-encoding axis in K-space, for example. Maximal separation of the center regions for the two echoes in K-space can be achieved, for instance, by reordering the acquisition of data in the two echoes. In another embodiment, the scan protocol is reordered along the first phase-encoding axis such that the center region of the first echo and the edge region of the second echo in K-space are acquired during an earlier portion of total data acquisition and the center region of the second echo and the edge region of the first echo in K-Space are acquired during a later portion of total data acquisition, or vice versa; that is, the order of the acquisitions can be reversed.

In a further embodiment, the scan protocol is in a form of a program that makes an information processing apparatus execute the method described above. The information process apparatus can be a personal computer or can be a part of an imaging instrument, such as a MRI. The program also can be embodied in or on a computer-readable recording medium.

BRIEF DESCRIPTION OF THE DRAWINGS

FIG. 6 compares, in the same subject as FIGS. 4 and 5, multi-slab CODEA and multi-slab dual-echo MRA/MRV without application of the K-space reordering scheme of the invention. a and b: TOF angiogram (a) and BOLD venogram (b), acquired using the CODEA with the echo-specific K-space reordering scheme. c and d: TOF angiogram (c) and BOLD venogram (d), acquired using the dual-echo angiography without K-space reordering (i.e., the conventional linearly-increasing k-space ordering was used in both echoes). An RF pulse with a flat excitation (flip angle 20°) was applied with no preparation pulse for the entire K-space regions in both echoes in c and d. Images in a and c are maximum-intensity projected over entire 3D volume and images in b and d are minimum-intensity projected over a slab with 17-mm thickness. Scan resolution for all the angiograms was 0.43×0.86×1.4 mm$^3$. Because a flat excitation pulse was applied for both echoes in c and d, the venous signals in d were relatively uniform. On the other hand, discontinuities were apparent in the arterial signals around the overlapping regions of the slab in c, which can be ascribed to the downstream blood saturation effects. Uniform vascular contrast with no discontinuity was observed in the MRA and MRV in the multi-slab CODEA acquisition (a and b).

DETAILED DESCRIPTION OF THE PREFERRED EMBODIMENTS

In MRA the arteries are depicted by virtue of their hyper-intense vascular signal, and the background tissue signal should be suppressed. The opposite is true in the MRV. To accommodate these conflicting requirements, the dual-echo scan parameters for the MRA and MRV should be individually adjustable.

To this end, dual-echo scan parameters compatible for both MRA and MRV vascular contrast can be achieved, according to the present invention, by exploring K-space characteristics and employing an echo-specific K-space reordering scheme. In particular, because the tissue contrast is determined predominantly by the K-space center characteristics, the vascular contrast for the MRA and MRV can be enhanced by maximally separating the K-space center acquired for the MRA from that for the MRV. Pursuant to the echo-specific K-space reordering scheme of the invention, the scan parameters for the MRA and MRV can be uncoupled and adjusted independently. For instance, the uncoupled scan parameters can be the same or can be different from each other.

Accordingly, the present invention provides for an improved dual-echo sequence MR imaging technique, which allows for simultaneously acquiring time-of-flight MR angiogram (MRA) and blood-oxygenation-level-dependent (BOLD) MR venogram (MRV), in a single MR acquisition. The simultaneous acquisition can refer to the acquisition of both MRA and MRV based on the application of a single pulse. As noted, MRA and MRV require conflicting scan conditions (e.g., excitation RF profile, flip angle, and spatial presaturation pulse) for their optimal image quality. The dual-echo sequence method of the invention reconciles this conflict by employing an echo-specific K-space reordering scheme to uncouple the scan parameter requirements for MRA and MRV. That is, MRA and MRV vascular contrast is enhanced by maximally separating the K-space centers acquired for the MRA and MRV and by adjusting and applying scan parameters that are compatible between the MRA and MRV.

In this manner the invention allows one to acquire a simultaneous dual-echo MRA and MRV with an image quality comparable to that for the conventional, single-echo MRA and MRV, acquired separately at two different sessions. Integration of this approach with tilted-optimized, nonsaturating excitation and multiple overlapping thin-slab acquisition techniques, provides seamless vascular continuity over a large coverage of the brain anatomy.

An extant technique for simultaneous acquisition of TOF angiogram and BOLD venogram advanced by Du and Jin (2008), supra, show reduced vascular contrast, for both TOF angiography and BOLD venography, as well as defects in vascular connectivity for TOF angiography. On the other hand, the present invention makes it possible to acquire both a TOF angiogram and a BOLD venogram at the same time, with minimal impact on vascular contrast and no defect in connectivity.

Pursuant to the invention, echo-specific K-space reordering in a dual echo sequence permits separate adjustment of scan parameters for each echo. In the examples below, this technique was tested for simultaneous acquisition of TOF arteriogram from the first echo and BOLD venogram from the second echo. The results showed that the image qualities from the inventive technique were comparable to those separately acquired with the conventional single-echo acquisition methods, which had never been achieved before.

This compatible dual-echo arteriovenography technique in MRI can be used as an vascular imaging tool for any organ. Because it enables one to acquire venogram as well as TOF angiogram with no additional scan time, the inventive technique can replace the conventional magnetic resonance TOF angiography that is routinely used in hospitals.

Excitation RF Pulses

Figure 1:
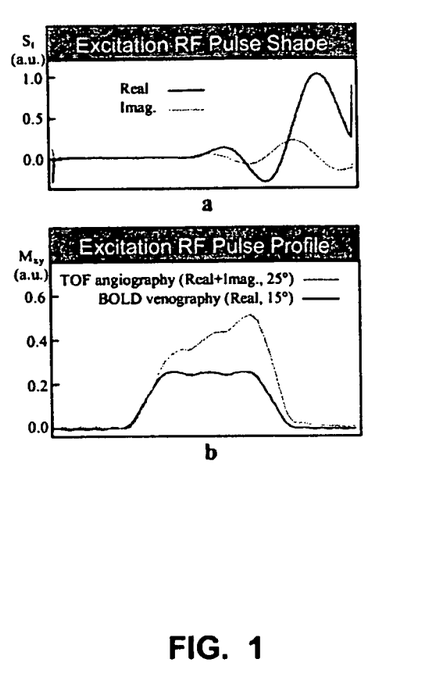
FIG. 1 is a graphical depiction of the shapes of real and imaginary parts of a minimum phase RF pulse, with ramped excitation profile. (a) Two different excitation RF pulse profiles are shown: One RF pulse, consisting of both the real and imaginary parts of the RF pulse with the flip angle of 25°, was used for TOF MRA (both single- and dual-echo acquisitions). (b) The other RF pulse, consisting of only the real part of the RF pulse with the flip angle of 15°, was used for BOLD MRV (again, both single- and dual-echo acquisitions).

As the spins of the flowing blood penetrate more distally downstream in an imaging slab, they repeatedly experience more RF excitations, and gradually they saturate. The blood signal in three-dimensional (3D) TOF MRA thus saturates and decreases proportionally to its spatial location, from upstream to downstream, within an imaging slab. This RF spatial saturation can be compensated and reversed by the application of excitation RF pulses with spatially varying ramp profile (TONE: tilted optimized nonsaturating excitation). In the examples detailed below, a minimum-phase RF pulse (to minimize TE for MRA) with a spatially varying ramp profile was designed following the Shinnar Le-Roux algorithm (FIG. 1a). The excitation profile was simulated and tested by means of a Runge-Kutta embedded numerical solution of the Bloch equations (FIG. 1b).

Compared to the arterial blood, the BOLD-based MRV vascular contrast is less likely to depend on blood movement. Furthermore, the ramped RF pulse may cause spatially varying, uneven background tissue signal intensity in the MRV. For these reasons, an excitation RF with a relatively flat profile is preferred in the MRV. The ramped RF pulse used for the MRA consists of the real and imaginary parts (darker and lighter gray lines, respectively, in FIG. 1a), and the real part corresponds to the conventional minimum-phase Shinnar Le-Roux pulse which generates a flat excitation profile (darker gray line in FIG. 1b). In the illustrative dual-echo sequence non-limiting implementation below, therefore, two different RF pulses were used for each of the MRA and MRV: one RF pulse with a ramped profile containing both the real and imaginary parts for the first echo (MRA), and the other RF pulse with a flat profile containing only the real part to the second echo (MRV). These two RF pulses are applied at two separate K-space regions in a 3D dataset, while the slab-select and refocusing gradients remain the same.

CODEA with Echo-Specific K-Space Reordering Scheme ("Divide and Conquer")

Figure 2:
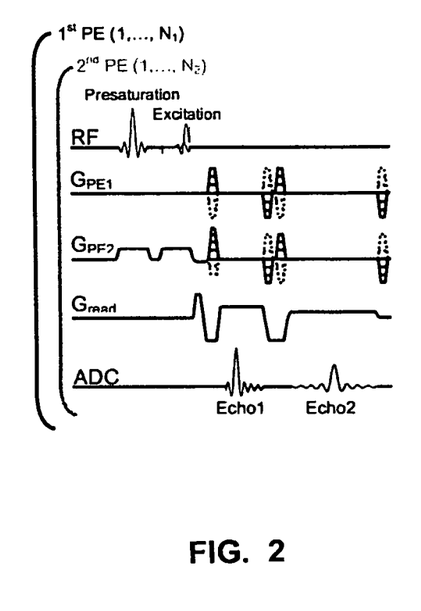
FIG. 2 is a pulse sequence diagram for dual-echo arteriovenography (CODEA). The diagram is for the acquisition of K-space center regions of the first echo, without including spoiler gradients, for sake of simplicity. A minimum phase RF pulse was used to keep the TE of the first echo as short as possible. According to the echo-specific K-space reordering scheme of the invention, the first and second phase-encoding gradients in the second echo were designed and applied independently from those in the first echo, i.e., they were rewound and applied again in the middle. Partial and full echoes were acquired for the first and second echoes, respectively. In the K-space center region in the second echo, only the real part of the excitation pulse was applied with no spatial pre-saturation pulse. The magnetization transfer contrast pulse (not shown) was applied instead of the pre-saturation pulse only in one of the 3D datasets per subject. The first phase encoding loop was located outside the second phase-encoding loop to minimize perturbations in the steady state condition, where $N_1$ and $N_2$ represent the total first and second phase-encoding lines, respectively.

The pulse sequence diagram for CODEA in one embodiment is shown in FIG. 2. With reference to the non-limiting examples, the first-order flow compensation was applied to both the slab-select and readout gradients. One of ordinary skill in the art can appreciate that the sequences of RF pulses need not be restricted to two. For example, the sequence of pulses can comprise two, three, four, or more pulses. According to the inventive echo-specific K-space reordering scheme, the first and second phase-encoding gradients in the second echo were designed and applied independently from those in the first echo (i.e., rewound and applied again in the middle). To enhance vascular-specific tissue contrast, the MRA and MRV were subjected to two different RF pulse-related settings (excitation pulse profile, flip angle, spatial presaturation pulse, and MTC pulse).

This application of the echo-specific RF pulse-related parameters is not feasible in a dual-echo setting when the first echoes for MRA and the second echoes for MRV are acquired along the same K-space line. The K-space acquisition ordering was altered, therefore, from the conventional (sequentially ascending) K-space ordering. To this end, various suitable reordering schemes can be applied. Reordering can be achieved, for example, by separately adjusting the phase-encoding steps, or gradients, in time scale for each of the echoes in the sequence of echoes, thereby to allow simultaneous acquisition of a TOF angiogram and a BOLD venogram with improved, or often optimal, scan parameters for each of the angiogram and venogram. As a result of the separate adjustment of the phase-encoding steps in such a reordering scheme, certain regions in K-space for each of the echoes can be adjusted, such that the echoes need not be acquired along the same K-space line or lines, and the scan parameters in certain regions in K-space for one echo can be adjusted independently of those for the other.

Figure 3:
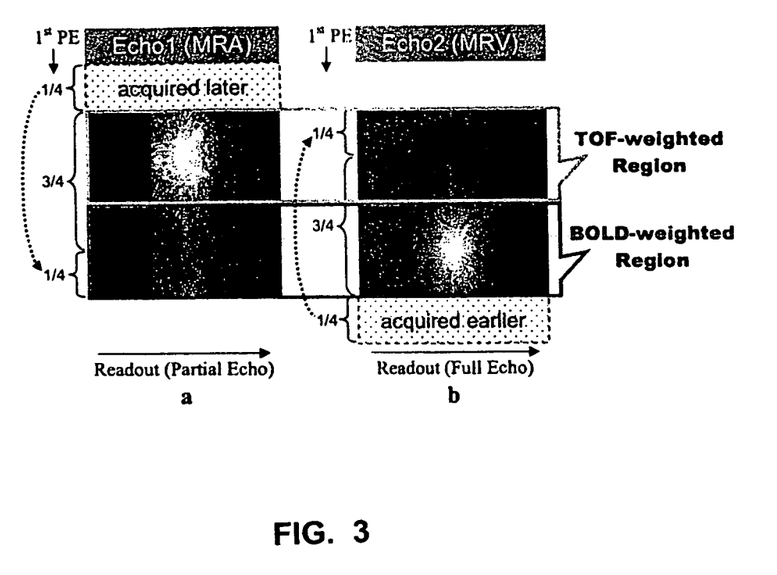
FIG. 3 illustrates a K-space distribution for CODEA according to the invention. In particular, cross sections of K-spaces are shown at the center along the second phase-encoding direction for the first echo (a) and the second echo (b). The K-space acquisition order was modified from the conventional, linearly-increasing order along the first phase-encoding direction. The initial ¼ of the total phase-encoding lines for the first echo was acquired at the end and the last ¼ of the total phase-encoding lines for the second echo was acquired at the beginning, as shown in a and b. The acquisition order shown in the figure can be reversed in the two echoes; that is, the last ¼ of the total phase-encoding lines for the first echo is acquired at the beginning and the initial ¼ of the total phase-encoding lines for the second echo at the end, such that the BOLD-weighted region is acquired prior to the TOF-weighted region. The same imaging outcome will result. When the K-space center region in the first echo was acquired (TOF-weighted MRA region), the excitation pulse with a spatially-varying ramp profile and a higher flip angle (20°-30° and the spatial presaturation pulse (or the MTC pulse, if specified) were applied to enhance the arterial contrast in the first echo. When the K-space center region in the second echo was acquired (BOLD-weighted MRV region), the excitation pulse with a flat profile and flip angle of 15° was applied with no preparation pulse, to improve the venous contrast in the second echo. Partial-echo and full-echo acquisitions were applied for the first and second echoes, respectively, as shown in a and b.

For example, one such scheme can be applied to separate maximally the center regions for the first and second echoes from each other, for example, along a phase-encoding axis in K-space (see in vivo data in FIGS. 3a and 3b). In this embodiment, the scan parameters are designed such that a center region of the first echo and an edge region of the second echo in K-space are acquired during the earlier portion of the total data acquisition operation, and a center region of the second echo and an edge region of the first echo in K-space are acquired during a later portion of the total data acquisition, or vice versa. Thus, the order of these two sets of acquisitions can be reversed.

The size of the region in the center and/or the edge in K-space can be of any suitable value. For example, pursuant to another embodiment, the initial ¼ of the K-space lines for the first echo is acquired at the end, while the final ¼ of the K-space lines for the second echo is acquired at the beginning along the first phase-encoding axis, as shown in FIGS. 3a and 3b. Alternatively, the region can be ⅕, ⅓, ½, of the K-space lines for each echo.

Additionally, because of the different regions of the respective echoes may be acquired either at an earlier or at a later portion of the acquisition, the sizes of the resulting regions for the respective echoes can be the same or different. For example, when the first echo provides a TOF MRA and the second echo provides a BOLD MRV, the size of the TOF region can be larger than that of the BOLD region (in the total acquisition). Thus, the former can be 60%, 70%, 80%, or more of the total acquisition. Alternatively, the size of TOF region can be smaller than that of the BOLD region. For example, the former can be 40%, 30%, 20%, or less of the total acquisition. Alternatively, the sizes of TOF and BOLD MRV regions can be substantially the same (e.g., 50%-50%).

In the particular embodiment illustrated in FIG. 3, thus, the RF pulse-related parameters for the MRA (ramped excitation pulse with a higher flip angle, spatial presaturation pulse, and MTC pulse) can be applied during the acquisition of the K-space center regions of the first echo (TOF-weighted region); those for the MRV (flat excitation pulse with lower flip angle, no preparation pulse), during the acquisition of the K-space center regions of the second echo (BOLD-weighted region). See FIG. 3.

Because the first phase-encoding direction typically can have a spatial resolution (K-space lines with higher frequencies) that is higher than the second phase-encoding direction, the K-space acquisition can be reordered along the first phase-encoding direction to increase the K-space separation between the two echoes (FIG. 3). Also, the first phase-encoding loop can be located outside the second phase-encoding loop in order to minimize any potential perturbations in the steady-state condition (FIG. 2). In this way, changes in the CODEA scan parameters can be required only once, in the middle, during the acquisition of an entire 3D dataset.

Simultaneous acquisition of MRA and MRV pursuant to the invention, without an increase in scan time and with minimal impact on the image quality, can be useful for both physiological studies and clinical diagnostic applications. An accurate assessment of some pathological conditions, such as Moyomoya disease and arterial venous malformation, can demand both arterial and venous vascular information. In a traditional contrast medium-enhanced angiography (X-ray or MR), the arteries and veins are distinguished because of their time-dependent dynamic contrast enhancement and are displayed in a cine mode. When there are variations in the arteriovenous circulation paths or technical limitations in capturing the artery or vein at specific scan time points, the arteries and veins may not be easily differentiable in a contrast-enhanced angiography. By contrast, with the CODEA technique of the invention the arteries and veins are imaged at the same time, which minimizes temporal or physiological variation in imaging the vessels, and are identified for their distinct vascular contrast (dark and bright) in two different datasets.

All commercial MRI systems have a number of common scan parameters available for optimization of scan protocols for specific tissues or organs. Among the more important scan parameters for vascular contrast are RF pulse excitation flip angle and profile, magnetization transfer contrast pulse, and spatial presaturation pulse. The dual-echo scan protocol is one of the scan protocols readily available in most MR systems, and it can be used for simultaneous acquisition of TOF angiogram (first echo) and BOLD venogram (second echo), as demonstrated by Du and Jin (2008).

The differences in intrinsic characteristics of TOF angiogram and BOLD venogram (i.e., blood vessels of hyperintensity and hypointensity, respectively) mean that the two angiograms require completely different settings for the important scan parameters, as noted above. In the conventional dual-echo scan protocol, the important scan parameters for vascular contrast are always coupled; hence, one parameter setting affects both echoes. The scan protocol for CODEA, pursuant to the invention, uncouples the scan parameter requirements in a timely manner, in that the earlier portion of the total acquisition is weighted for TOF angiogram and the later portion for BOLD venogram, or vice versa, through the inventive echo-specific K-space reordering scheme depicted in FIG. 3.

In accordance with the invention, therefore, MRI users can adjust the important scan parameters independently. As illustrated below, more particularly, the important scan parameters can be individually adjusted such that: for the first and second echoes, RF pulse excitation flip angle=25° and 15°, respectively; excitation profile=ramped and flat; magnetization transfer contrast pulse=on and off (only in one of the datasets, for safety); and spatial pre-saturation pulse=on and off. See Barnes et al., *Proc. Int'l. Soc. Mag. Reson. Med.* 16: 2231 (2008), and present FIG. 6 for a demonstration of the effect of the RF pulse excitation flip angle, FIG. 6 for the effect of the excitation profile, FIG. 7 for the effect of magnetization transfer contrast pulse, and FIGS. 4 and 6 for the effect of spatial pre-saturation pulse.

NON-LIMITING EXAMPLES

All experiments were performed on a Siemens 3T system, product of Siemens Medical Systems (Iselin, N.J.), with a vendor-supplied, circularly-polarized head RF coil. Three normal male volunteers who provided informed consent were scanned in this study which was approved by the Institutional Review Board. Voxel-localized shimming was performed with a vendor-supplied shim module based on a 3D phase map. A total of six 3D datasets were acquired with imaging time of about 1 hour in each subject: four dual-echo MRA and MRV and two single-echo MRA and MRV, with varying numbers of acquisition slabs, K-space reordering schemes, and with and without a MTC pulse.

1. Single-Slab, Dual-Echo MRA/MRV (CODEA)

A single-slab, dual-echo arteriovenogram (MRA and MRV) was acquired using the K-space reordering scheme (FIG. 3). Imaging parameters were: time to repeat (TR)=50 ms, matrix size=512×208×64, corresponding field of view=220×179×88 mm³, and number of averages=1. A partial Fourier sampling (75%) was employed, to reduce the scan time, and a slice oversampling (18%) was used to avoid a wrap-around artifact along the second phase-encoding direction. The scan time for a 3D dataset was 9.8 minutes. The TE and acquisition bandwidth were 3.2 ms and 150 Hz/pixel, respectively, in the first echo, and 24 ms and 34 Hz/pixel, respectively, in the second echo. A partial echo sampling (67%) was used in the imaginary parts of the RF pulse (darker and lighter gray lines in FIG. 1a) were used in this acquisition. On the other hand, the K-space center region in the second echo (for the BOLD-weighted MRV region in FIG. 3) was acquired with a relatively flat-profile RF excitation with flip angle of 15° (darker gray line in FIG. 1b). Only the real part of the RF pulse (darker gray line in FIG. 1a) was used in the second-echo K-space acquisition. MTC pulse was not used to keep the specific absorption rate (SAR) low, unless specified otherwise. The utility and effect of an MTC pulse were tested separately in a later dual-echo sequence.

2. Conventional Single-Slab, Single-Echo MRA and MRV

As the comparison reference to the dual-echo MRA and MRV (CODEA), the conventional single-echo TOF MRA and single-echo BOLD MRV were acquired in two separate imaging sessions. The first-order flow compensation was applied in the slab-select and readout gradients. The scan parameters of the single-echo MRA were determined to be identical to those for the first echo (TOF-weighted regions) of the CODEA and applied to the entire single-echo K-space. Likewise, the scan parameters of the single-echo MRV were the same as those for the second echo (BOLD-weighted regions) of the CODEA, and they again were applied to the entire single-echo K-space.

3. Multi-Slab CODEA

One of the advantages of the inventive CODEA technique is to provide a multi-slab, dual-echo MRA and MRV with seamless vascular continuity over a large coverage of the brain anatomy. To demonstrate this capability, CODEA was acquired in two overlapping slabs according to the multiple overlapping thin-slab acquisition (MOTSA) mode which is commonly used in 3D TOF MRA. The scan parameters were identical to those for the single-slab CODEA except for the matrix size=512×208×32, corresponding field of view=220×179×44 mm³, and acquisition of two overlapping slabs with a gap between the two slabs of −5 mm. In the multi-slab CODEA, the imaginary part of the ramped excitation RF pulse (for the TOF-weighted regions) was reduced by half, thus decreasing the first-echo flip angle range from 20°-30° to 22.5°-27.5°. This reduction would improve the vascular intensity continuity between the slabs.

4. Multi-Slab, Dual-Echo MRA/MRV without K-Space Reordering

The aforementioned double-slab, dual-echo MOTSA with the echo-specific K-space reordering was compared to the double-slab, dual-echo MOTSA without the K-space reordering. In the absence of the K-space reordering, the K-spaces for both the MRA and MRV were acquired according to the conventional (i.e., sequentially increasing) phase-encoding mode. The excitation RF profile was flat with the flip angle of 20° which was an intermediate value between those for the first (25°) and second (15°) echoes. No spatial presaturation pulse was applied to either echo. The remaining scan parameters were identical to the double-slab, dual-echo MOTSA with the echo-specific K-space reordering (i.e., CODEA technique). The final scan setting was similar to that reported by Du and Jin (2008), supra, except for two different acquisition bandwidths in the two echoes and for the acquisition of a full echo for the second echo.

5. Single-Slab CODEA with Magnetization Transfer Contrast (MTC) Pulse

A single-slab CODEA was additionally acquired with an MTC pulse and TR of 58 ms. Other scan parameters were the same as those for the aforementioned single-slab CODEA without an MTC. No spatial presaturation pulse was applied for this acquisition.

6. Reconstruction and Data Analysis

Each 3D raw dataset was Fourier-transformed to generate 3D images with the matrix size of 512×416×204 for the single-slab acquisition and 512×416×102 for the multi-slab (double-slab) acquisition. The voxel dimensions became isotropic following a zero filling procedure. Venous contrast in the single- and dual-echo MRV was enhanced using phase-mask filtering. MRA images were displayed in maximum-intensity projections on the transaxial, sagittal, and coronal planes, whereas MRV images were displayed in minimum-intensity projections on the transaxial and coronal planes.

The signal intensities were measured over an arterial region (only for MRA), a tissue region devoid of detectable blood vessels, and the background region outside the brain. From these measurements, the contrast to noise ratio (CNR) in the MRA arterial vessels and the signal to noise ratio (SNR) of tissue in the MRV were computed. To reduce potential motion-related errors in measurements of the arterial CNR in multiple 3D datasets, the arterial regions were selected sufficiently large by including the whole cross section and then averaging the highest four pixel intensities. In the MRV, the tissue SNR instead of the venous CNR was used as a measure of the image quality. Although the MRV tissue SNR and venous CNR are comparable because of the hypointense vascular signal, the tissue SNR measurement is more robust than the venous CNR measurement. All measurements were repeated in three different slice offset positions at −20, 0, and 20 mm from the slab center in the single-slab acquisition or the center of total imaging volume in the multi-slab acquisition. Thus, in three subjects, a total of nine repeated measurements were available for data analysis. Using these multiple measurements, the effect of the ramped excitation was assessed. Patterns were tested for statistical significance with Wilcoxon signed rank test at the significance level of 0.05.

Single-Slab CODEA vs Conventional Single-Slab, Single-Echo MRA and MRV

Figure 4:
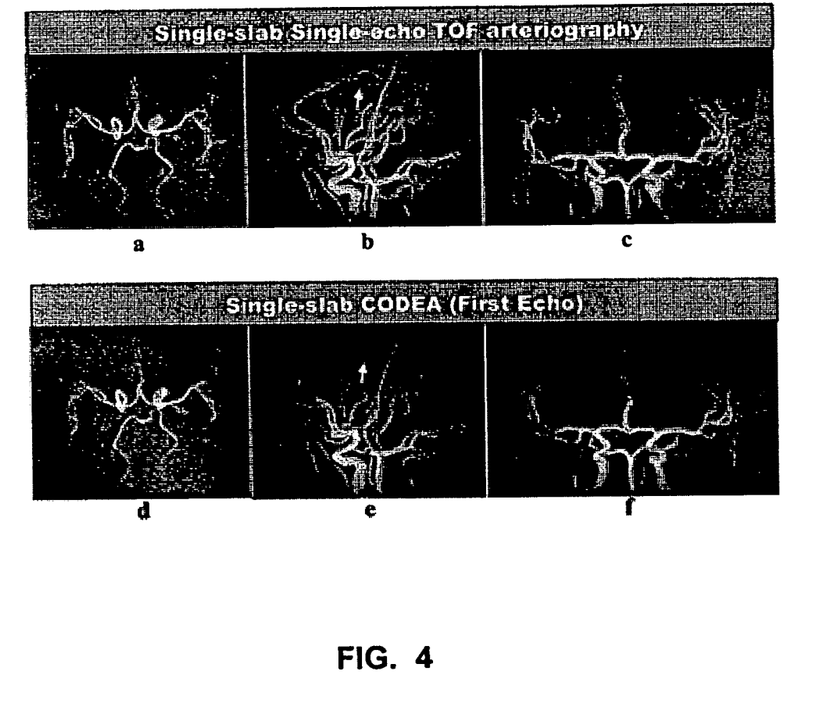
FIG. 4 compares TOF angiograms acquired via conventional, single-echo and CODEA methods. Shown are single-echo TOF angiograms at MIP along axial (a), sagittal b), and coronal (c) directions, over the entire 3D volume, and (first-echo) CODEA TOF angiograms at MIP along axial (d), sagittal (e), and coronal (f) directions, again over the entire 3D volume. Scan resolution for all the angiograms is 0.43×0.86×1.4 mm$^3$. Overall, the single-echo and CODEA MRA's were comparable in image quality. The arrows in b and e identify a small downstream artery, with a reduced vascular contrast in the CODEA MRA.

No signal intensity discontinuity was observed in the K-spaces of the first and second echo regions in the single-slab CODEA (FIGS. 3a and 3b). The MRA's acquired using the CODEA technique were qualitatively comparable to those using the single-echo technique for all subjects (FIG. 4). A slight reduction in the vascular contrast was observed in some small downstream arteries (arrows in FIG. 4e). The relative percent. CNR's of the CODEA MRA to the single-echo MRA were 93±18, 99±16, and 78±2%, measured at −20 (upstream), 0, and 20 mm (downstream) from the slab center, respectively (CNR values ranged 10-63). There was no statistically significant difference between the CNR values from the CODEA and the single-echo MRAs overall (p=0.173). The vascular signal intensity shown in the sagittal and coronal projection images (FIGS. 4e and f) was relatively uniform throughout the direction of blood movement, indicating that the expected signal degradation due to blood saturation was well compensated by the application of the ramped excitation pulse only to the K-space center region. Also tested was the utility of the spatial presaturation pulse for suppressing venous signals in MRA. The spatial presaturation pulse was applied to the entire K-space region for the single echo MRA while only to the central K-space region of the first-echo for the CODEA. In either case, the spatial presaturation pulse was effective in suppressing venous signals (FIG. 4), accentuating the hyperintense arterial vascular signal in the MRA.

Figure 5:
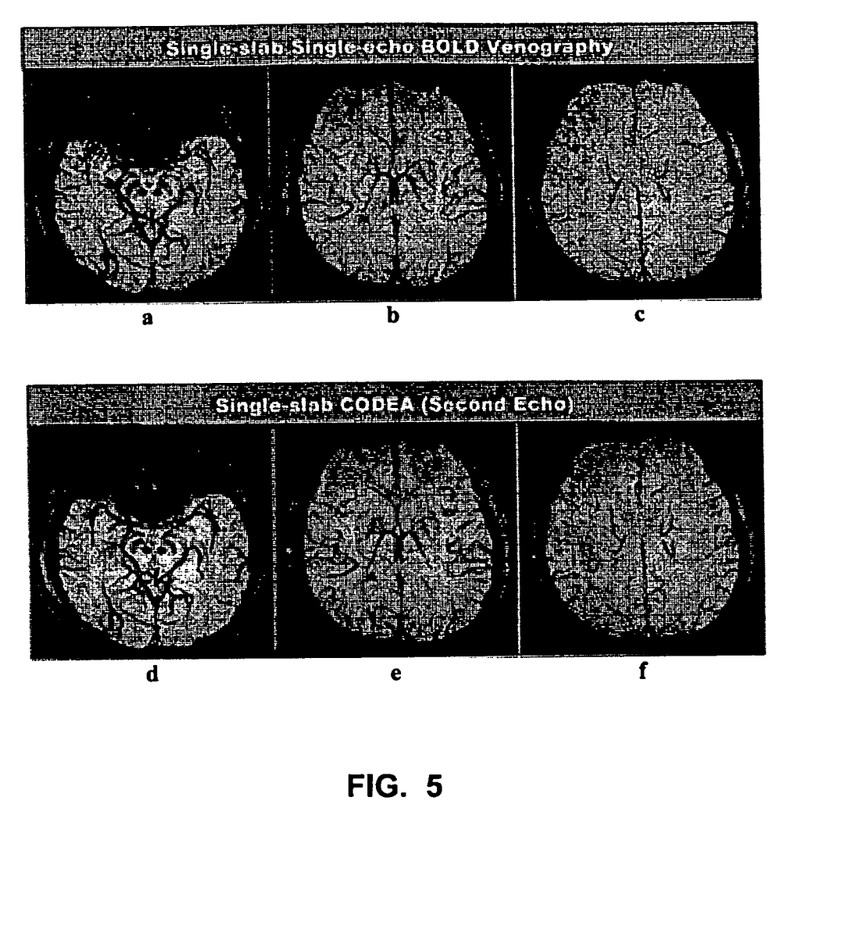
FIG. 5 compares BOLD venograms acquired using conventional, single-echo and CODEA methods for the same subject addressed in FIG. 4. a-c: The conventional single-echo BOLD venogram at three different locations. d-f: The (second-echo) CODEA BOLD venogram at the same locations as a-c. The scan resolution for all the angiograms is 0.43×0.86×1.4 mm$^3$. All images are minimum-intensity projected over 10 mm. The single-echo and CODEA MRVs were equivalent in image quality.

MRV images acquired with the single echo and CODEA at three different positions are shown in FIG. 5. The CODEA MRV and single-echo MRV were equivalent in their image quality for all study subjects, even in the locations closer to the slab edge (FIG. 5f) where the flip angle difference between the K-space center and edge regions was the highest (FIG. 1b). The tissue SNR values in the CODEA MRV measured at −20, 0, and 20 mm from the slab center were 19.9±2.9, 22.0±4.5, and 21.1±1.4, respectively, while those in the single-echo MRV were 19.6±3.4, 21.1±4.8, and 19.6±0.9, respectively. There was consistent increase in the tissue SNR value from the CODEA MRV compared to that from the single-echo MRV at all the three locations (1, 4, and 8% at −20, 0, and 20 mm from the slab center) (p<0.05), but the difference was visually indistinguishable (FIG. 5). This small difference in the tissue SNR values between the CODEA and single-echo MRVs (<10% overall) suggests that the characteristics of the second echo in the CODEA MRV were predominantly determined by the flat excitation pulse applied only to the central K-space region.

Multi-Slab CODEA vs Multi-Slab Dual-Echo MRA/MRV without K-Space Reordering

Figure 6:
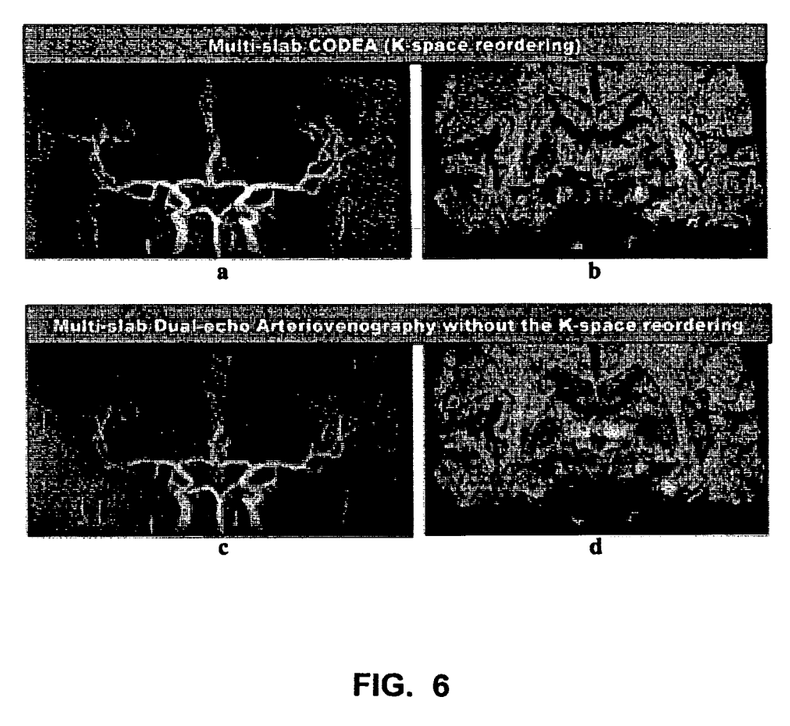

Multi-slab (double-slab) CODEA images displayed in the coronal maximum intensity projection of MRA (FIG. 6a) and coronal minimum intensity projection of MRV (FIG. 6b), demonstrated uniform signal intensity and seamless vascular continuity in the overlapping and adjacent slices in the slabs. Venous signals in the MRA were effectively suppressed by the spatial presaturation pulse applied to the K-space center region of the first echo (FIG. 6a). In contrast, the MRA acquired in the dual-echo MRA/MRV without K-space reordering showed spatially varying signal intensities in the overlapping and adjacent arterial vessels (FIG. 6c). This signal intensity variation was likely due to the downstream spin saturation effect that could not be compensated with the use of the flat excitation RF pulse. Two additional drawbacks of the MRA without K-space reordering that we observed in all our tested subjects were a reduced vascular contrast (because of decreased inflow enhancement with the use of intermediate flip-angle) and signals from large veins (which could not be eliminated without an appropriate spatial presaturation pulse) (FIG. 6c). The relative percent CNR of the MRA without K-space reordering to the CODEA MRA was 78±9, 79±6, and 83±14%, measured at −20, 0, and 20 mm from the center of the total imaging volume, respectively, indicating a significant decrease in CNR in the MRA without K-space reordering (p<0.05).

Unlike the MRA, no considerable differences in MRV image quality were observed between the double-slab CODEA (FIG. 6b) and double-slab dual-echo MRA/MRV without K-space reordering schemes (FIG. 6d). The two techniques demonstrated equally uniform and continuous MRV signal intensity in the overlapping and adjacent vessels. The tissue SNR values in the CODEA measured at −20, 0, and 20 mm from the center of the total imaging volume were 14.4±1.3, 16.3±1.9, and 14.0±2.4, respectively, and those in the dual-echo MRA/MRV without K-space reordering techniques were 15.1±0.7, 15.4±1.9, and 14.3±1.5, respectively. There was no statistically significant difference (p=0.95).

Single-Slab CODEA with MTC Pulse

Figure 7:
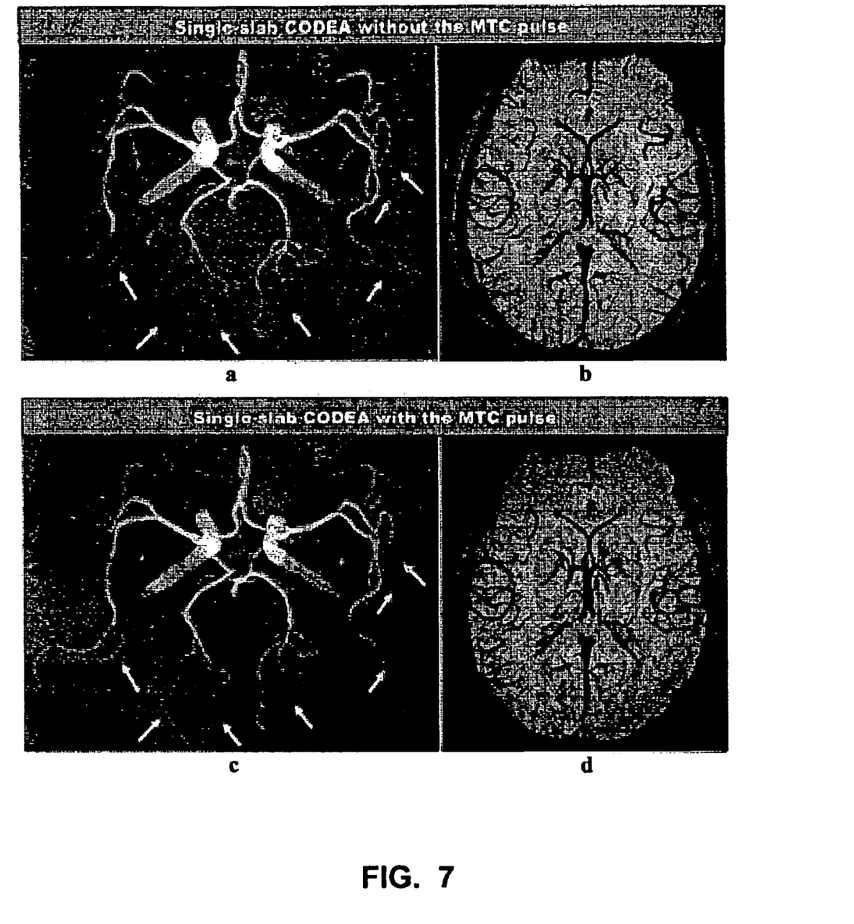
FIG. 7 compares CODEA without and with the MTC pulse in a different subject from that of FIGS. 4-6. a and b: TOF angiogram (a) and BOLD venogram (b), acquired using the CODEA without the MTC pulse. c and d: TOF angiogram (c) and BOLD venogram (d), acquired using the CODEA with the MTC pulse. Images in a and c are maximum-intensity projected over entire 3D volume, while images in b and d are minimum-intensity projected over 10 mm. The MTC pulse improved the visualization of small vessels in TOF angiograms (arrows in c), with no apparent effect on the BOLD venogram (d).

The TR value was slightly lengthened when the MTC pulse was used (58 ms with vs 50 ms without the MTC). Nevertheless, the visualization of small arteries was improved with the use of the MTC pulse for all tested subjects (FIGS. 7a and 7c). The signal intensity and SNR of the background tissue in the CODEA MRA with the MTC pulse were reduced by 13±2% and 15±5%, respectively, compared to those without the MTC pulse (FIG. 7) (p<0.05). On the other hand, the effect of the MTC on the CODEA MRV was negligible (FIGS. 7b and 7d): the background tissue signal intensity increased by 4±5% with the MTC pulse (p<0.05), but no significant difference in the tissue SNR (21.4±3.1 with vs 21.0±2.9 without MTC, p=0.44). Tissue T1 is 1-1.5 seconds at 3 T and the tissue signal intensity is expected to increase by approximately 6% with the TR increase (from 50 to 58 ms) at the given flip angle (15°). This calculation, along with our background tissue signal measurement, again confirms that the MTC had little effect on the CODEA MRV.

These results show that techniques commonly used in conventional 3D TOF MRA and MRV, such as MOTSA, can be readily incorporated into the CODEA because constraints in determining the dual-echo scan parameters are reduced by the use of the echo-specific K-space reordering scheme, pursuant to the invention. Compared to the single-slab acquisition, the MOTSA technique, which combined the advantages of 2D and 3D acquisitions, improved the visualization of small blood vessels (data not shown). On the other hand, the tissue SNR (or CNR of hypointense venous vessels) in the CODEA MRV was higher in the single-slab acquisition than in the MOTSA, as quantified in the experiments above and as expected from the increased excitation volume. This trade-off in the MRA and MRV vascular CNR, which is associated with the number of the slabs, cannot be resolved in the CODEA method.

These results also show that the MTC pulse selectively suppressed the background tissue signal in the MRA, thus enhancing the arterial contrast (FIG. 7c). The MTC, on the other hand, had little effect on the venous contrast in the MRV (FIG. 7d). A practical limitation of using MTC pulse in 3T MRA is that it increases the SAR. MTC pulse power has been reduced by weighting far more pulse powers in the center than the periphery of the K-space regions. In accordance with the invention, a modified MTC could be incorporated into the CODEA to improve the arterial vascular contrast without substantially increasing the SAR.

What is claimed is:

1. A dual-echo method of simultaneously acquiring a magnetic resonance angiography and a magnetic resonance venography, comprising the steps of:
   (A) separating the center regions for a first echo and a second echo, respectively, in K-space; and then
   (B) applying to the center regions pre-defined K-space scan parameters that are specific to the center regions, whereby said angiography and venography are acquired from said first and second echoes, respectively,
   wherein said scan parameters for said first echo are selected independently from those for said second echo.

2. The method of claim 1, wherein the step (B) further comprises reordering said scan parameters such that a center region of said first echo and an edge region of said second echo in K-space are acquired during an earlier portion of total data acquisition and a center region of said second echo and an edge region of said first echo in K-space are acquired during a later portion of the total data acquisition, or vice versa.

3. The method of claim 1, wherein said scan parameters comprise radio frequency pulse excitation flip angle, radio frequency pulse excitation profile, magnetization transfer contrast pulse, spatial presaturation pulse, or a combination thereof.

4. The method of claim 1, wherein the center regions are maximally separated.

5. A non-transitory computer-readable recording medium, that has recorded thereon a program that makes an information processing apparatus execute a method of claim 1.

6. The program of claim 5, wherein the information process apparatus is a part of an imaging instrument.

7. The method of claim 1, wherein said scan parameters for said first echo are different from those for said second echo.

\* \* \* \* \*

UNITED STATES PATENT AND TRADEMARK OFFICE
CERTIFICATE OF CORRECTION

PATENT NO.        : 8,676,296 B2  Page 1 of 1
APPLICATION NO. : 13/062187
DATED             : March 18, 2014
INVENTOR(S)      : Park et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 361 days.

Signed and Sealed this
Twenty-ninth Day of September, 2015

Michelle K. Lee
*Director of the United States Patent and Trademark Office*